(12) United States Patent
Naito

(10) Patent No.: US 6,294,520 B1
(45) Date of Patent: *Sep. 25, 2001

(54) MATERIAL FOR PASSAGE THROUGH THE BLOOD-BRAIN BARRIER

(76) Inventor: Albert T. Naito, 2776 Cibola, Costa Mesa, CA (US) 92626

(*) Notice: Subject to any disclaimer, the term of this patent is extended or adjusted under 35 U.S.C. 154(b) by 0 days.

This patent is subject to a terminal disclaimer.

(21) Appl. No.: 07/341,487

(22) Filed: Mar. 27, 1989

(51) Int. Cl.[7] ................................................ A61K 31/435
(52) U.S. Cl. ........................ 514/23; 514/2; 514/904; 514/270; 514/922
(58) Field of Search ........................ 514/23, 2, 904, 514/905, 270, 922; 424/439, 9.1

(56) References Cited

U.S. PATENT DOCUMENTS

| | | | |
|---|---|---|---|
| 4,025,650 | * 5/1977 | Gans et al. | 424/804 |
| 4,042,687 | * 8/1977 | Gans et al. | 424/804 |
| 4,053,589 | * 10/1977 | Gans et al. | 424/804 |
| 4,543,262 | * 9/1985 | Michnowski | 426/804 |
| 4,639,465 | * 1/1987 | Pollack et al. | 514/419 |
| 4,824,850 | * 4/1989 | Bodor | 514/270 |
| 4,832,971 | * 5/1989 | Michnowski | 426/804 |
| 4,859,475 | * 8/1989 | Michnowski | 426/804 |
| 4,959,227 | * 9/1990 | Amer | 426/804 |
| 4,965,074 | * 10/1990 | Leeson | 514/343 |

FOREIGN PATENT DOCUMENTS

| | | |
|---|---|---|
| 03052810 | * 3/1991 | (JP) . |
| 05339148 | * 12/1993 | (JP) . |
| 652012 | * 5/1995 | (WO) . |

* cited by examiner

*Primary Examiner*—Ralph Gitomer
*Assistant Examiner*—Devesh Khare
(74) *Attorney, Agent, or Firm*—Edward E. Roberts; Howard M. Eisenberg

(57) ABSTRACT

A material which has the ability to effect it's passage, at least in part, and the ability to transport other materials through the blood-brain barrier which includes any one or more pure sugars or pure amino sugars from the group consisting of meso ethritol, zylitol, D(+) galactose, D(+) lactose, D(+) xylose, dulcitol, myo-insoitol, L(-) fructose, D(-) mannitol, sorbitol, D(+) glucose, D(+) arabinose, D(-) arabinose, celloboise, D(+) maltose, D(+) raffinose, L(+)rhamnose, D(+) melibiose, D(-) ribose, adonitol, D(+) arabitol, L(-) arabitol, D(+) fucose, L(-) fucose, D(-) lyxose, L(+) lyxose, L(-) lyxose, D(+) glucosamine, D mannosamine, and D galactosamine; and any one or more amino acids from the group consisting of arginine, asparagine, aspartic acid, cysteine, glutamic acid, glycine, histidine, leucine, methionine, phenylalanine, proline, serine, threonine, glutamine, lysine, tryptophan, tyrosine, valine, and taurine. For use in the research or treatment of a subject that material is combined with one or more of the substances beta carotene, xanthophyll, lecithin, calcium, somatostatin, vasopressin, endorphin, enkephalin, acetyl-L-carnitine, GABA, dynorphin, L-tryptophan, choline, thiamine, pyridoxine, niacin, L-arginine, hydroxyproline, NGF, methionine, cystine, potassium, phosphorus, chlorine, sodium, vitamins A, B, C, D and E, and selenium.

17 Claims, No Drawings

MATERIAL FOR PASSAGE THROUGH THE BLOOD-BRAIN BARRIER

This invention relates to materials and methods for passing, and transporting other substances, through the blood-brain barrier.

BACKGROUND OF THE INVENTION

If one accepts the premise that most physiological functions are controlled by the brain and the medium of that control is electrical signalling as an incident to chemical activity in the brain, then it seems logical to conclude that an absence in the brain of the chemicals required for that activity can result in signal failure and consequent physiological disfunction. It is possible also to conclude that a genetic trait which interferes with such chemical activity can result in signal failure and disfunction. It is also possible to conclude that the presence of a given substance in the brain may interfere chemically with the proper generation of control signals.

Such considerations, the search for an understanding of the mechanism of drug dependence, drunkenness, Alzheimer's disease, schizophrenia and other disorders, some associated with the brain and others apparently not, have lead many researchers to look for a relation between such disorders and availability of chemicals in the brain. The medical literature includes descriptions that comparison of brain tissue of persons who succumbed to a given disease with that of persons who died of unrelated causes suggest a relation between a given chemical and the disease. Thus lack of lithium has been mentioned in connection with schizophrenia and lack of neuropeptides has been mentioned in connection with Alzheimer's disease.

Studies in that area, the chemical treatment of brain cancers, and other studies and procedures are hampered by the difficulty in introducing chemicals into the brain because of what is commonly called the blood-brain barrier. The blood vessels of the brain are formed by cells which are more closely packed than are the vessels elsewhere in the body. That fact and the action of the astrocyte cells account for the fact that many materials are difficult to introduce into the glia of the brain. In some cases the only way that researchers had of getting those materials was to form a hole in the subject's skull and inject the desired material into the brain.

This invention relates to the transportation of material through that blood-brain barrier.

SUMMARY OF THE INVENTION

It is an object of the invention to provide novel substances and methods which are useful in conducting research with animal and human subjects into the causes and cure of certain disorders and for the treatment of those disorders.

A related object is to provide substances of that kind which can be utilized by ingestion by a test subject or patient.

Another object is to provide a vehicle and a method for transporting substances across the blood-brain barrier.

Another object is to provide particular substances which are suitable for the study, and in some cases the treatment, of specific disorders. One of those disorders is loss of hair.

One related object is to provide a substance which, at least for some subjects, has the effect of restoring hair.

These and other objects and advantages of the invention which will hereinafter appear, are realized by the provision of materials which appear to pass through the blood-brain barrier and are capable restoring impeded neuro-transmitter function and apparently of transporting other materials through the barrier or at least facilitating their utilization in the chemical processes of the body. The material that provides those actions is a combination of one or more of a number of "pure" sugars and or pure amino sugars from the group consisting of one or more of a number of amino acids. The sugars are meso erythritol, xylitol, D(+) galactose, D(+) lactose, D(+) xylose, dulcitol, myo-inositol, L(−) fructose, D(−) mannitol, sorbitol, D(+) glucose, D(+) arabinose, D(−) arabinose, cellobiose, D(+) maltose, D(+) raffinose, L(+) rhamnose, D(+) melibiose, D(−) ribose, adonitol, D(+) arabitol, L(−) arabitol, D(+) fucose, L(−) fucose, D(−) lyxose, L(+) lyxose, L(−) lyxose, D(+) glucosamine, D mannosamine, and D galactosamine. The term "pure" as applied to sugar herein means crystalline purity, 98 or 99 percent pure. The requirement for high purity is based upon both a need for purity and the fact that the character of impurities is unknown and some can negate the effectiveness of the sugar or the amino acids.

The amino acids are glutamine, lysine, arginine, asparagine, aspartic acid, cysteine, glutamic acid, glycine, histidine, leucine, methionine, phenylalanine, proline, serine, threonine, tryptophan, tyrosine, valine, and taurine. The amino acids may be those found in common foodstuffs such as orange juice, clam chowder, soy bean soup, sheep milk, and others, but for uniform and more predictable result it is preferred that the amino acid be incorporated in pure crystalline form.

Both the proportions in which those materials are combined, and of any added test substances materials, and the quantity of the combination varies with the nature and weight of the test subject. In the case of humans an excessive amount of any of the listed sugars can cause nausea, heat sensation, flushing, and ringing of the ears. More than 6 grams of sugar at one time may produce the adverse side effects listed above. Except that excess amounts of amino acid may have harmful effect on subjects afflicted with certain illness, there appears to be no upper limit to the amount of amino acid that is safely ingested at least by humans.

Haklitch and Naito, in attempting to apply the base material to the treatment of alcohol induced drunkenness in humans, have discovered that certain proportions and dosages appear to be both effective to restore motor functions in humans and to be safe for human consumption. The same proportions of sugar and amino acids, and the same dosage in combination with beta carotene have been found to be effective in arresting hair loss and in restoring hair growth. However, different proportions and dosages are preferred in other cases. Drunkenness and hair loss occur in primarily in adults. The invention is applicable to humans and animals of various sizes. The base material is a combination of sugar and amino acid which is effective to permit transportation of other materials into the glia of the brain past the blood brain barrier. The preferred dosage is, in general, the minimum amount of base material which permits such transportation, one eighth gram of sugar and 10 to 50 milligrams of amino acid is probably the minimum for adults and medium to large animals when the amount of material to be transported is minimal. In most cases it will be desireable to transport more than minimal quantities, the actual amount being related to the subject's weight. The examples set out below assume a weight range which extends from less than a pound for small animals and four pounds in the case of premature human infants to 350 pound, active athletes.

That the base material or some component of it, after having been ingested and entering the blood stream, or having been introduced directly into the blood stream, does actually cross the blood-brain barrier is most readily shown in a test of a person whose motor functions have been very obviously impaired by ingestion of alcohol. Ingestion by that subject of the base material has the effect of restoring the subject's motor functions in a matter of seconds notwithstanding that the alcohol level in the subject's blood remains high.

Evidence has been found that ingesting other substances with the basic combination of sugar and amino acid so that they coexist in the blood stream can result in facilitation of the use of the added material by the body. In one example, adding beta carotene, or xanthophyll, has the effect of increasing the growth of hair and of replacing greyness with original hair color without yellowing the skin. The chemistry of hair restoration by the addition of beta carotene is not known. The fact that it produces the result without the inclusion of carcinogenic material makes it useful for treatment of baldness and certainly useful as a research material. Usefulness, at least as a preferred test or research material, is true too of other combinations of specific substances, lecithin, calcium, somatostatin, vasopressin, acetyl-L-carnitine, GABA, dynorphin, vitamins, electrolytes and various minerals and other materials with the base sugar and amino acid materials.

DESCRIPTION OF THE PREFERRED EMBODIMENTS

The basic material of the invention is one that passes the blood brain barrier and which has the ability to transport other materials across that barrier. It comprises the combination of one or more of a number of "pure" sugars or "pure" amino sugars with one or more of a number of amino acids. The sugars are meso erythritol, zylitol, D(+) galactose, D(+) lactose, D(+) xylose, dulcitol, myo-insoitol, L(-) fructose, D(-) mannitol, sorbitol, D(+) glucose, D(+) arabinose, D(-) arabinose, celloboise, D(+) maltose, D(+) raffinose, L(+) rhamnose, D(+) melibiose, D(-) ribose, adonitol, D(+) arabitol, L(-) arabitol, D(+) fucose, L(-) fucose, D(-) lyxose, L(+) lyxose, and L(-) lyxose. The term "pure" as applied to sugar herein means crystalline purity, 99 percent pure. The amino sugars are D(+) glucosamine, D mannosamine, and D galactosamine. In the case D(+) glucosamine, pure means about 99 percent pure. In the case of D mannosamine, and D galactosamine, pure means about 98 percent pure. Here-in-after the amino sugars are included in the term "sugar." The requirement for high purity is based upon both a need for purity and the fact that the character of impurities is unknown and some can negate the effectiveness of the sugar or the amino acids.

The amino acids are glutamine, lysine, arginine, asparagine, aspartic acid, cysteine, glutamic acid, glycine, histidine, leucine, methionine, phenylalanine, proline, serine, threonine, tryptophan, tyrosine, valine, and taurine. The amino acids may be those found in common foodstuffs such as orange juice, clam chowder, soy bean soup, sheep milk, and others, but for uniform and more predictable result it is preferred that the amino acid be incorporated in pure crystalline form.

In the case of research on human subjects and in the treatment of human subjects, the preferred form of the invention is the combination in the base material of any one or more of the listed sugars and any one or more of the listed amino acids in a quantity such that for each measure of the sugar between 2.5 and 6 grams there is an accumulation of effective amounts to a total of about 480 milligrams or more.

As indicated above, no upper limit to the permissible amount of amino acid has been found. However, medical authorities recommend that persons with certain kinds of ailments avoid ingesting massive doses of amino acid.

The quantity above which additional quantities of amino acids have no effect when combined with 2.5 to 6 grams of sugar was found by Haklitch and Naito to between 2000 and 3000 mg when the objective was to restore motor functions to drunken subjects. No such threshold of effectiveness has been found for other applications. The lower limit for observable beneficial result is very low, five to ten milligrams of amino acid. Within the list of amino acids, arginine, tryptophan, and tyrosine are preferred.

EXAMPLE OF BASE MATERIAL

Example 1

The combination of from about 0.2 grams to six grams of pure sugar selected from, or consisting of a combination of sugars from, the group consisting of meso erythritol, zylitol, D(+) galactose, D(+) lactose, D(+) xylose, dulcitol, myo-insoitol, L(-) fructose, D(-) mannitol, sorbitol, D(+) glucose, D(+) arabinose, D(-) arabinose, celloboise, D(+) maltose, D(+) raffinose, L(+)rhamnose, D(+) melibiose, D(-) ribose, adonitol, D(+) arabitol, L(-) arabitol, D(+) fucose, L(-) fucose, D(-) lyxose, L(+) lyxose, L(-) lyxose, D(+) glucosamine, D mannosamine, and D galactosamine with 10 to 3000 mg of amino acid consisting of any combination of, or any one of, the group of amino acids consisting of glutamine, lysine, arginine, asparagine, aspartic acid, cysteine, glutamic acid, glycine, histidine, leucine, methionine, phenylalanine, proline, serine, threonine, tryptophan, tyrosine, valine, and taurine.

Hair Growth

It has been demonstrated that certain materials are useful in retarding loss of hair. A number of proprietary products are available commercially which claim some success both in reducing hair loss and in restoring hair. They are applied externally and it is thought that they serve as neuroreceptors at the surface of hair follicle cells. The material of the invention is beta carotene which, when introduced into glia may serve as a neurotransmitter to signal hair follicles to action. Tests demonstrate that when beta carotene is ingested with a material such as that described above that will cross the blood-brain barrier. In one test, thirty mg of beta carotene taken daily for forty five days with 2500 mg of fructose in 250 cc of orange juice resulted in arrest of hair loss at the user's hairline and growth of new hair in the area of his crown. The subject, whose natural hair color was black, turning grey, had virtually only black head and body hair at the end of the forty five day test.

Tests indicate that the base material, sugar and amino acid in the quantities described above are effective to result in transportation of beta carotene, and other substances for about one half hour. Whether that is because the base material remains in the blood for that period or produces an effect in the brain that lasts for that period is not known. However, because of that effect the beta carotene need not be ingested with the base material but can be ingested at a point removed in time. There appears to be no critical dosage of beta carotene. Because it is ingested and because the recommended daily amount is 5000 IU, that quantity is now considered to be the preferred minimum. No acceleration of hair restoral has been observed when the amount of beta carotene is increased above 20,000 IU so that is now considered to be the upper limit above which increased cost provides no benefit.

Other Research and Treatment Applications

The invention provides novel materials for research into the understanding and/or treatment and the possible treatment of disorders where an attempt is to be made to transport chemical substances past the blood-brain barrier. To realize that objective, the invention comprises the combination of a material that will pass the blood-brain barrier and any non-carcinogenic material having apparent utility in connection with the treatment of the disorder being investigated. In preferred form the material that will pass the blood-brain barrier is a sugar and amino acid combination as described above and the added material is a vitamin or mineral or electrolyte who effect is to be tested. Some examples of specifically preferred materials are listed below.

Other Examples

The following several examples are intended to describe mid range proportions and doses of test and treatment materials for human subjects. Striped of quantity figures, they are examples of substance combinations that will pass the blood brain barrier in the testing and treatment of higher order animals and humans.

Example 2

For research into and or treatment of baldness:
the sugar and amino acid combination described in example 1 above; and
165 to 15000 IU and preferably about 30 mg beta carotene or xanthophyll.

Example 3

For research into and or treatment of Alzheimer Disease:
the sugar and amino acid combination described in example 1 above;
10 mg to 12,000 mg and preferably about 2500 mg of lecithin;
120 to 2500 mg and preferably about 1000 mg of calcium;
5 to 1000 mg and preferably about 10 mg somatostatin;
5 to 1000 mg and preferably about 10 mg vasopressin; and
1 to 500 mg and preferably about 10 mg acetyl-L-carnitine.

Example 4

For research into and or treatment of Huntington's disease:
the sugar and amino acid combination described in example 1 above;
2.5 to 1000 mg and preferably about 1000 GABA; and
5 to 1000 mg and preferably about 10 mg dynorphin.

Example 5

For research into and or treatment of depression, insomnia or chronic pain:
the sugar and amino acid combination described in example 1 above including 2 to 750 mg, and preferably about 500 mg, L-tryptophan; and
10 mg to 12000 mg and preferably about 2500 mg lecithin or 13 to 5000 mg and preferably about 1000 mg choline;
0.2 to 125 mg and preferably about 1.5 mg thiamine;
0.2 to 125 mg and preferably about 2 mg pyridoxine; and
16 to 25 mg and preferably about 20 mg niacin.

Example 6

For research into and or treatment of addiction to alcohol, heroine, cocaine or nicotine, anxiety, bulimia, anorexia nervosa, phobia, panic disorder, obsessive compulsive disorder, and attention deficit hyperactivity disorder:
the sugar and amino acid combination described in example 1 above including 15 to 5700 mg and preferably about 2500 mg of one or a combination of L-arginine and hydroxyproline.

Example 7

For research into and or treatment of brain damage, stroke, spinal cord injury and autism:
the sugar and amino acid combination described in example 1 above;
10 mg to 12000 mg, and preferably about 2400 mg, lecithin; and
0.5 to 50, and preferably about 10 mg, Nerve Growth Factor (NGF) polypeptide.

Example 8

For research into and or treatment of muscular dystrophy, Lou Gehrig's disease and cerebral palsy:
the sugar and amino acid combination described in example 1 above including 6 to 2500 mg and preferably about 550 mg methionine;
2.5 to 920 mg and preferably about 550 mg cystine;
120 to 2500 mg and preferably about 1000 mg calcium;
155 to 2350 mg and preferably about 2000 mg potassium chloride or 155 to 4000 mg and preferably about 2500 mg potassium gluconate;
1 to 5 mg and preferably about 3 mg boron;
60 to 800 mg and preferably about 120 mg phosphorus;
13 to 5000 mg and preferably about 1000 mg chlorine;
50 to 5800 mg and preferably about 2500 sodium chloride; and
5 to 1000 mg and preferably about 10 mg dynorphin.

Example 9

For research into and or treatment of osteoporois or bone damage:
the sugar and amino acid combination described in example 1 above,
155 to 2350 mg and preferably about 2000 mg potassium chloride or 155 to 4000 mg and preferably about 2500 mg potassium gluconate;
60 to 1200 mg and preferably about 800 mg phosphorus;
50 to 5800 mg and preferably 2500 mg sodium chloride;
14 to 1000 IU and preferably about 400 IU vitamin D;
50 to 18000 mg and preferably about 60 mg vitamin C;
1 to 5 mg and preferably about 3 mg boron; and
120 to 2500 mg and preferably about 1500 mg calcium carbonate.

Example 10

For research into and or treatment of incontinence and heart muscle disorders:

the sugar and amino acid combination described in example 1 above;

155 to 2350 mg and preferably about 2000 mg potassium chloride or 155 to 4000 mg and preferably about 2500 mg potassium gluconate;

120 to 2500 mg and preferably about 1000 mg calcium;

14 to 1000 IU and preferably about 400 IU vitamin D; and 50 to 18000 mg and preferably about 60 mg vitamin C.

Example 11

For research into and or treatment of cancers of the lung:

the sugar and amino acid combination described in example 1 above;

25 to 35 mg and preferably about 30 mg beta carotene;

180 to 10000 IU and preferably about 5000 IU of vitamin A;

18 to 400 IU and preferably about 30 IU vitamin E; and 2 to 200 mcg and preferably about 10 mcg selenium.

Example 12

For research into and or treatment of poor memory, stress, headache and stuttering:

the sugar and amino acid combination described in example 1 above; and 10 to 12000 mg and preferably about 2500 mg lecithin or chorine.

Example 13

For research into and or treatment of pain, hypertension, cardiac arrhythmias, Parkinson's Disease, pre-menstrual syndrome (PMS), and shock:

the sugar and amino acid combination described in example 1 above which includes about 1000 mg or more of L-tryptophan; and 10 to 12000 mg and preferably about 2500 mg lecithin or chorine.

Example 14

For research into and or treatment of acne and wrinkles:

the sugar and amino acid combination described in example 1 above;

180 to 10000 IU and preferably about 5000 IU vitamin A;

25 to 35 mg and preferably about 30 mg beta carotene; and 50 mg to 18 grams and preferably about 1 gram of vitamin C.

Example 15

For research into and or treatment of manic depression:

the sugar and amino acid combination described in example 1 above including 2 to 2000 mg and preferably about 1000 mg tryptophan;

1 to 1000 mg endorphin; and 1 to 1000 mg enkephalin.

Example 16

For research into and or treatment of the general symptoms of aging:

2 to 4 grams of one or more of the sugars listed in example 1 above;

the recommended daily requirement (RDA) of vitamins A, B-1, niacin, B-2, B-6, B-12, C, D, E, D-biotin, pathothenic acid and folic acid;

about 40 to 50 mg vitamin K;

about 1000 mg beta carotene;

the recommended daily requirement of the minerals: calcium, phosphorus, iodine, iron, magnesium, copper, and zinc;

about 5 to 15 mg of each of chromium, selenium, and molybdenum;

2 to 3 mg manganese;

35 to 40 mg potassium;

30 to 40 mg chloride;

2 to 3 grams lecithin; and 400 to 2000 mg choline;

the recommended daily requirement of the amino acids: lysine, histidine, leucine, methionine, phenylalanine, tryptophan, tyrosine and valine;

about 1 gram of each of the amino acids glutamine, aspartic acid, glutamic acid, threonine, proline and serine;

15 to 6000 mg and preferably about 800 mg arginine;

1 to 500 mg and preferably about 250 mg asparagine;

11 to 500 mg and preferably about 400 mg glycine;

2 to 900 mg and preferably about 90 mg cysteine; and 1 to 500 mg and preferably about 500 mg taurine.

Example 17

For research into and or treatment of diabetes:

the sugar and amino acid combination described in example 1 above including 2 to 2000 mg and preferably about 1000 mg tryptophan and 11 to 4100 mg and preferably 1000 mg tyrosine; and 10 to 12000 mg and preferably about 2500 mg lecithin or chorine.

Example 18

For research into and or treatment of abnormal or undesirable blood chemistry particularly in relation to cholesterol and plasma, HDL and LDL the sugar and amino acid combination described in example 1 above; and 500 to 6000 mg and preferably about 1000 mg of niacin.

Example 19

For research into and or treatment of migraine headache and comatose condition:

the sugar and amino acid combination described in example 1 above which includes about 1000 mg or more of L-tryptophan; and 10 to 12000 mg and preferably about 2500 mg lecithin or chorine.

Example 20

For ingestion by athletes in training, the upper range of the substances listed in Example 16 above.

I claim:

1. A method for passing and transporting substances through the blood-brain barrier, said method comprising the oral administration to a human subject of a saccharide component sufficient to open the blood-brain barrier of the subject and an amino acid material to be thereafter transported across the blood-brain barrier and received in the brain of the subject, wherein the amino acid material comprises at least one of the amino acids selected from the group consisting of glutamine, lysine, arginine, asparagine, aspartic acid, cysteine, glutamic acid, glycine, histidine, leucine, methionine, phenylalanine, proline, serine, threonine, tyrosine, valine, and taurine.

2. The method according to claim 1 which further includes administering to said subject a treatment material suitable to treat a bodily affliction such that said material coexists in said subject's body with the saccharide component.

3. The method according to claim 1 wherein said saccharide component is comprised of any one or more sugars selected from the group consisting of: meso erythritol, xylitol, D(+) galactose, D(+) lactose, D(+) xylose, dulcitol, myo-inositol, L(−) fructose, D(−) mannitol, D(+) glucose, D(+) arabinose, D(−) arabinose, cellobiose, D(+) maltose, D(+) raffinose, L(+) rhamnose, D(+) melibiose, D(−) ribose, adonitol, D(+) arabitol, L(−) arabitol, D(+) fucose, L(−) fucose, D(−) lyxose, L(+) lyxose, and L(−) lyxose.

4. A method for eliciting a therapeutic effect of a therapeutic chemical substance other than a sugar or an amino acid, comprising administering the substance to a patient in need thereof, orally co-administering a sugar and an amino acid in an amount sufficient to elicit the therapeutic effect of the substance, and permitting the substance to exert its therapeutic effect.

5. The method according to claim 4 wherein the administration of the therapeutic substance and the administration of the sugar and the amino acid are timed so that they coexist in the bloodstream of the patient at levels higher than before the administration thereof.

6. The method according to claim 4 wherein the therapeutic substance is administered within one half hour following administration of the sugar and amino acid.

7. The method according to claim 4 wherein the sugar is selected from the group consisting of meso erythritol, lactose, xylose, dulcitol, myo-inositol, D(−) mannitol, D(+) glucose, D(+) arabinose, D(−) arabinose, cellobiose, D(+) maltose, D(+) raffinose, L(+) rhamnose, D(+) melibiose, D(−) ribose, adonitol, D(+) arabitol, D(−) arabitol, D(+) fucose, L(−) fucose, D(−) lyxose, and L(−) lyxose.

8. The method of claim 4 wherein the patient is a human.

9. The method of claim 4 wherein the therapeutic substance exerts its therapeutic effects by an action within the brain.

10. The method of claim 4 wherein the therapeutic effect is selected from the group consisting of arresting hair loss, restoring hair growth, and restoring original hair color.

11. The method of claim 4 wherein the amino acid is selected from the group consisting of glutamine, lysine, arginine, asparagine, aspartic acid, cysteine, glutamic acid, glycine, histidine, leucine, methionine, phenylalanine, proline, serine, threonine, tyrosine, valine, and taurine.

12. The method of claim 4 which further comprises permitting either or both of the saccharide component and the amino acid material to cross the blood-brain barrier and enter the brain.

13. The method of claim 4 wherein said therapeutic substance is selected from the group consisting of lecithin, calcium, acetyl-L-carnitine, vitamins, electrolytes, and minerals.

14. The method of claim 4 wherein the therapeutic effect is enhancing memory.

15. The method of claim 14 wherein the substance is lecithin or choline.

16. The method of claim 4 wherein the therapeutic effect is treating Alzheimer's disease.

17. The method of claim 16 wherein the substance is a combination of lecithin, calcium, somatostatin, vasopressin, and acetyl-L-carnitine.

* * * * *